United States Patent [19]

Terasawa et al.

[11] 4,359,479

[45] Nov. 16, 1982

[54] CHEWING GUM CONTAINING AN ENERGY-RICH PHOSPHATE COMPOUND

[75] Inventors: Masatoshi Terasawa, Tokorozawa; Hisashi Ishikawa, Tokyo; Takuo Uemura, Fujimi, all of Japan

[73] Assignee: Lotte & Co., Ltd., Tokyo, Japan

[21] Appl. No.: 226,740

[22] Filed: Jan. 21, 1981

[30] Foreign Application Priority Data

Mar. 11, 1980 [JP] Japan ................................. 55-29788

[51] Int. Cl.³ .............................................. A23G 3/30
[52] U.S. Cl. ...................................................... 426/3
[58] Field of Search ....................................... 426/3–6; 424/48, 50, 57, 94

[56] References Cited

U.S. PATENT DOCUMENTS

| | | | |
|---|---|---|---|
| 2,197,718 | 4/1940 | Conner | 426/4 |
| 3,011,949 | 12/1961 | Bilotti | 424/48 |
| 3,075,884 | 1/1963 | Bilotti et al. | 426/5 |
| 3,085,048 | 4/1963 | Bush | 424/48 |
| 3,629,395 | 12/1971 | Litchfield et al. | 424/48 |
| 3,751,561 | 8/1973 | Wildi et al. | 424/48 |
| 3,932,608 | 1/1976 | Anderson et al. | 424/48 |
| 4,088,788 | 5/1978 | Ream | 426/3 |
| 4,100,301 | 7/1978 | Friello | 426/3 |
| 4,151,270 | 4/1979 | Ream et al. | 426/3 |
| 4,233,288 | 11/1980 | Cornell | 426/5 |

OTHER PUBLICATIONS

Chem. Absts., vol. 94, 1981, P90061, p. 393, "Dentifrices Containing ATPase Activating Polypeptides".

*Primary Examiner*—Jeanette M. Hunter

[57] ABSTRACT

A chewing gum containing an energy-rich phosphate compound is disclosed. The phosphate compound is extremely unstable and releases its "−P" bond readily with giving off high energy and therefore is preferably used in combination with fat. The chewing gum according to the invention is suitable for recovery of fatigue after sports or hard work.

8 Claims, No Drawings

CHEWING GUM CONTAINING AN ENERGY-RICH PHOSPHATE COMPOUND

FIELD OF THE INVENTION

This invention relates to a chewing gum containing an energy-rich phosphate compound.

BACKGROUND OF THE INVENTION

There are many types of energy-rich phosphate compounds having relatively low energy of 2 to 4 Kcal/mole such as glucose-6-phosphate or high energy of 12.8 Kcal/mole such as pyruvic acid in the enol form, which have in general a common characteristic of an energy-rich phosphate bonding, defined as "−P". In this context, the term "energy-rich phosphate compound" means all types of phosphate compounds having high energy in the level of 6 to 15 Kcal/mole, including ATP (adenosine triphosphate), ADP (adenosine diphosphate), AMP (adenosine monophosphate), CP (creatine phosphate) and the like. The energy-rich phosphate compound releases its bonding "−P" readily with giving off high energy and therefore has been known as a quickly effective energy source.

Furthermore, the energy-rich phosphate compound, especially ATP, is extremely unstable and readily decomposable. For protection thereof a method of stabilizing the ATP in an aqueous solution has been known as disclosed in the Japanese Patent Publication 38270/71.

On the other hand, for the purpose of obtaining quickly effective fatigue-recovery action various types of chewing gums such as a sports gum are commercially available, which contain a quickly effective sugar, such as glucose, as well as vitamines, amino acids, minerals and others. However, there has not yet been known a chewing gum containing an energy-rich phosphate compound for giving off high energy, suited for a quickly effective chewing gum, particularly the sports gum.

SUMMARY OF THE INVENTION

A general object of the invention is, therefore, to provide a high energy releasable chewing gum having fatigue recovery effect, especially upon playing sports or hard work, through effective absorption of quickly released energy via intestine after chewing.

A principal object of the invention is to provide a chewing gum containing an energy-rich phosphate compound which comprises a chewing gum base and the energy-rich phosphate compound incorporated thereto, optionally together with fat, in addition to usual chewing gum additives.

DETAILED DESCRIPTION OF THE INVENTION

As described in the foregoing, the energy-rich phosphate compound used in the invention contains high energy in the level of 6 to 15 Kcal/mole and readily releases its "−P" bond with giving off the high energy. As an example of the phosphate compound, there may be mentioned ATP, ADP, AMP, CP or the like, among which the ATP being most preferred. Other materials containing the energy-rich compound, such as yeast powder, may also be used directly.

An amount of the energy-rich phosphate compound, especially ATP, to be used in the chewing gum according to the invention may be widely varied but generally be in the range of 0.01 to 10%, preferably 0.05 to 1.0% by weight based on the product chewing gum in consideration of various factors, such as energy level, decomposability, taste and others of the phosphate compound.

As stated in the foregoing, the ATP is extremely unstable and readily decomposable, especially in the presence of moisture, and therefore may be used optionally in combination with fat preferably in the form of powder for stabilizing purpose. Since the chewing gum contains only low moisture less than 2%, the ATP may be, of course, incorporated without stabilization, differing from other high moisture agents such as an injection solution, chemicals or foodstuffs. Preferably, however, the ATP may be stabilized by the method according to the Japanese Patent Publication 38270/71 or conventional methods for protecting unstable substances such as encapsulation or double- or triple-coating with hydrophobic materials. If the water content of the foodstuff is less than 3%, the ATP is rather stable and is not always necessary to be stabilized. Above the water content of 7% on the other hand, the ATP should be protected by any stabilizing means because of its higher susceptibility to decomposition. In accordance with the invention the energy-rich phosphate compound, especially ATP, may be added in admixture with the fat preferably in the powdery form or the fat may be added immediately before addition of the ATP in order to increase stability of the ATP in the chewing gum. The reason why the addition of the fat may increase the stability of the energy-rich phosphate compound has not exactly been known but presumably resides in that the fat reduces viscosity of the chewing gum so that heat generated during the gum kneading is protected from being transferred directly to the ATP and that the ATP may be dispersed throughout the chewing gum under the protected condition with the fat. Another advantage of the addition of the fat is to control the rate of elution of the energy-rich phosphate compound from the gum upon chewing. For the purpose of stabilization an amount of the fat used is in the range of 0.5 to 20%, preferably 1 to 5% by weight based on the product chewing gum. Such amount of the fat may be incorporated in any form, such as liquid, powder or granules, although the powdery form is most preferred when the fat is used in admixture with the ATP.

Since the energy-rich phosphate compound, especially ATP, is extremely unstable and readily decomposable, the time of its addition should be taken into consideration for obtaining the maximum stabilizing effect with the minimum amount. Preferably the energy-rich phosphate compound, especially ATP, may be incorporated at the possibly latest stage of the chewing gum manufacturing, for example, at the final finishing stage after addition of flavors, wherein the fat is more preferably added in admixture with the ATP or immediately before the addition of the ATP. Upon the addition of ATP, it is more effective to keep the temperature of the chewing gum at less than 60° C., preferably less than 50° C. for inhibiting decomposition of the ATP.

In order to prepare the chewing gum according to the invention, of course, any other known gum base materials and additives may be included and any conventional methods and apparatus may be employed, except that the time of addition of the energy-rich phosphate compound as well as the moisture content of the chewing gum should be taken into consideration. In addition to the energy-rich phosphate compound, especially ATP, any other nourishment, such as amino acids (for example, essential amino acids), vitamines (for example, vitamines B1, B2, C, D, E, nicotinic acid amide), minerals (for example, calcium, potassium, sodium salts) and others may be incorporated in the well-balanced condition for providing a well-nourished chewing gum having quickly effective high energy. In this case the addition of about 0.01 to 10.0% by weight of amino acids, about 0.001 to 5.0% by weight of vitamines and about 0.001 to 5.0% by weight of minerals based on the product chewing gum may provide the well-balanced and nourished chewing gum. For example, the combination of (1) the energy-rich phosphate compound, (2) amino acids, (3) vitamines and (4) minerals hereinbelow illustrated may result in the following effects, respectively:

| Combination | Effect obtained |
| --- | --- |
| (1) + (2) + (3) | Recovery of fatigue after hard work. |
| (1) + (3) | Recovery of muscle fatigue after playing sports. |
| (1) + (2) + (3) | Persistent fighting spirit for study. |
| (2) + (3) + (4) | Good effect on malnourishment, on weak body and as a nutritive tonic. |
| (1) + (3) | Good for sports, drive, trip, business. |
| (1) + (2) + (3) + (4) | Good for an overweight or underweight person. |
| (1) + (2) + (3) + (4) | Good for a too-busy person having no regular meal times. |
| (2) + (3) + (4) | Good for obtaining a well-balanced body. |
| (1) + (2) + (3) + (4) | Useful for emergency application. |
| (1) + (2) + (3) + (4) | Suitable as a refreshment for a growing child. |

The chewing gum containing the energy-rich phosphate compound according to the invention was prepared by use of the following formulation:

| Formulation 1 | | |
| --- | --- | --- |
| Gum base | 21.6% | by weight |
| Glucose | 32.4 | by weight |
| Sucrose | 32.4 | by weight |
| Starch hydrolyzate | 10.8 | by weight |
| ATP | 0.3 | by weight |
| Vitamines (B1, B2, C, D, E, Nic. A.) | 0.3 | by weight |
| Amino acids (miscellaneous) | 1.1 | by weight |
| Minerals (Ca—, K—, Na— salts) | 1.1 | by weight |
| Total | 100.0 | by weight |

| | Formulations 2 to 5 | | | | |
| --- | --- | --- | --- | --- | --- |
| | 2 | 3 | 4 | 5 | |
| Gum base | 20.4 | 20.4 | 20.4 | 20.4% | by weight |
| Sucrose | 65.0 | 65.0 | 65.0 | 63.0 | by weight |
| Starch hydrolyzate | 7.0 | 7.0 | 7.0 | 8.0 | by weight |
| Softener | 0.7 | 0.7 | 0.7 | 0.7 | by weight |
| (Powdery) fat | 1.0 | 3.0 | 5.0 | 5.0 | by weight |
| Flavor | 0.8 | 0.8 | 0.8 | 0.8 | by weight |
| ATP | 0.1 | 0.3 | 0.5 | 1.0 | by weight |
| Others | 5.0 | 2.8 | 0.6 | 1.1 | by weight |
| Total | 100.0 | 100.0 | 100.0 | 100.0 | by weight |

It will be appreciated that the preferred embodiment of the invention was illustrated hereinabove with ATP as the energy-rich phosphate compound but any other energy-rich compounds may be utilized in the same manner without departing from the scope of the invention.

What is claimed is:

1. A chewing gum with high energy, which comprises a chewing gum base and at least one phosphate compound incorporated thereto and selected from the group consisting of adenosine triphosphate (ATP), adenosine diphosphate (ADP), adenosine monophosphate (AMP) and creatine phosphate (CP), in addition to other chewing gum additives including sweeteners, softeners and flavors.

2. A chewing gum with high energy according to claim 1, which further comprises a fat for stabilizing the phosphate compound.

3. A chewing gum with high energy according to claim 1 or 2, wherein the phosphate compound is incorporated in an amount of 0.01 to 10% by weight based on the product chewing gum.

4. A chewing gum with high energy acording to claim 2, wherein the fat is incorporated in an amount of 0.05 to 1.0% by weight based on the product chewing gum.

5. A chewing gum with high energy according to claim 2, wherein the fat is incorporated in an amount of 0.5 to 20% by weight based on the product chewing gum.

6. A chewing gum with high energy according to claim 2, wherein the fat is incorporated in an amount of 1 to 5% by weight based on the product chewing gum.

7. A chewing gum with high energy according to any one of claims 2, 4 or 5, wherein the fat is incorporated in the form of powder.

8. A process for preparing the chewing gum with high energy according to claim 1 or 2, which comprises incorporating at least one phosphate compound selected from the group consisting of ATP, ADP, AMP and CP at the final stage of chewing gum manufacturing while maintaining the water content of the chewing gum at less than 3%.

* * * * *